(12) United States Patent
Smink et al.

(10) Patent No.: US 9,348,005 B2
(45) Date of Patent: May 24, 2016

(54) INTERVENTIONAL OR NON-INTERVENTIONAL INSTRUMENT FOR USE IN AN MRI APPARATUS

(75) Inventors: Jouke Smink, Best (NL); Steffen Weiss, Hamburg (DE)

(73) Assignee: Koninklijke Philips N.V., Eindhoven (NL)

( * ) Notice: Subject to any disclaimer, the term of this patent is extended or adjusted under 35 U.S.C. 154(b) by 105 days.

(21) Appl. No.: 14/240,602

(22) PCT Filed: Aug. 29, 2012

(86) PCT No.: PCT/IB2012/054425
§ 371 (c)(1),
(2), (4) Date: Feb. 24, 2014

(87) PCT Pub. No.: WO2013/035013
PCT Pub. Date: Mar. 14, 2013

(65) Prior Publication Data
US 2014/0187914 A1 Jul. 3, 2014

Related U.S. Application Data

(60) Provisional application No. 61/531,248, filed on Sep. 6, 2011.

(30) Foreign Application Priority Data

Sep. 6, 2011 (EP) .................................... 11180171

(51) Int. Cl.
| | | |
|---|---|---|
| *A61B 5/05* | (2006.01) | |
| *G01R 33/28* | (2006.01) | |
| *G01R 33/36* | (2006.01) | |
| *A61B 5/01* | (2006.01) | |
| *A61B 5/042* | (2006.01) | |
| *A61B 5/00* | (2006.01) | |
| *A61B 10/02* | (2006.01) | |
| *A61M 25/01* | (2006.01) | |

(Continued)

(52) U.S. Cl.
CPC ................ *G01R 33/287* (2013.01); *A61B 5/01* (2013.01); *A61B 5/042* (2013.01); *A61B 5/6852* (2013.01);

(Continued)

(58) Field of Classification Search
CPC ....... A61B 10/0233; A61B 5/01; A61B 5/042; A61B 5/055; A61B 5/6852; G01R 33/287; G01R 33/54; G01R 33/3685; G01R 33/288; A61M 25/0127
USPC ............................ 600/407–435; 324/318–322
See application file for complete search history.

(56) References Cited

U.S. PATENT DOCUMENTS 4,041,435 A 8/1977 Gaia
4,341,218 A * 7/1982 U .................................. 606/195

(Continued)

FOREIGN PATENT DOCUMENTS

| WO | 02074164 A1 | 9/2002 |
|---|---|---|
| WO | 2008032249 A2 | 3/2008 |

OTHER PUBLICATIONS

Zanchi, Maria G. et al "An Optically Coupled System for Quantitative Monitoring of MRI-Induced RF Currents into Long COnductors", IEEE Trasactions on Medical Imaging, vol. 29, No. 1, Jan. 2010. pp. 169-178.

(Continued)

*Primary Examiner* — Sanjay Cattungal

(57) ABSTRACT

An interventional or a non-interventional instrument like a catheter, a surgical device, a biopsy needle, a pointer, a stent or another invasive or non-invasive device, like a position marker, or a surface or local coil like a head coil is disclosed, wherein these instruments are provided with an MR-safe RF transmission line or cable (2, 3) for connecting the instrument with related RF transmit/MR receive units or other signal processing units for operating the instrument during an MR imaging or MR examination of an examination object. Basically, MR safety is obtained or increased by means of a plurality of fuses (6) which are serially connected into the transmission line or cable (2, 3).

15 Claims, 1 Drawing Sheet

(51) Int. Cl.
 *G01R 33/54* (2006.01)
 *A61B 5/055* (2006.01)

(52) U.S. Cl.
 CPC ........ *A61B 10/0233* (2013.01); *A61M 25/0127* (2013.01); *G01R 33/3685* (2013.01); *G01R 33/54* (2013.01); *A61B 5/055* (2013.01); *G01R 33/288* (2013.01)

(56) References Cited

U.S. PATENT DOCUMENTS

| | | |
|---|---|---|
| 4,928,384 A | 5/1990 | Gurevich |
| 5,140,295 A | 8/1992 | Vermot-gaud et al. |
| 5,332,990 A | 7/1994 | Duerr et al. |
| 2005/0027191 A1 | 2/2005 | Uutela et al. |
| 2010/0217368 A1 | 8/2010 | Dinsmoor et al. |
| 2011/0037471 A1 | 2/2011 | Nozaki |

OTHER PUBLICATIONS

Nordbeck, Peter et al "Measuring RF-Induced Currents inside Implants: Impact of Device Configuration on MRI Safety of Cardiac Pacemaker Leads", Magnetic Resonance in Medicine, vol. 61, 2009, pp. 570-578.

Anandh Ravi, "Efficacy of Multi-Channel Array Coil for Pediatric Cardiac Magnetic Resonance Imaging", A Thesis Presented to the Graduate Faculty of the University of Akron, December 2008, p. 1-64.

* cited by examiner

INTERVENTIONAL OR NON-INTERVENTIONAL INSTRUMENT FOR USE IN AN MRI APPARATUS

CROSS-REFERENCE TO PRIOR APPLICATIONS

This application is the U.S. National Phase application under 35 U.S.C. §371 of International Application No. PCT/IB2012/054425, filed on Aug. 29, 2012, which claims the benefit of U.S. Provisional Patent Application No. 61/531, 248, filed on Sep. 6, 2011 and European Patent Application No. 11180171.8, filed on Sep. 6, 2011. These applications are hereby incorporated by reference herein.

FIELD OF THE INVENTION

The invention relates to an interventional or a non-interventional instrument for use during an MR imaging or MR examination of an examination object, like a catheter, a surgical device, a biopsy needle, a pointer, a stent or another invasive or any non-invasive device, like a position marker, or a surface coil or local coil like a head coil, wherein these instruments are provided with an RF transmission line or cable for connecting the instrument with related RF transmit units, MR receive units or other especially remote signal receiving and/or signal processing units for operating the instrument during an MR imaging or MR examination of an examination object.

BACKGROUND OF THE INVENTION

In an MRI apparatus (or an MR scanner), an examination object, usually a patient, is exposed within the examination space of the MRI apparatus to a uniform main magnetic field ($B_0$ field) so that the magnetic moments of the nuclei within the examination object tend to rotate around the axis of the applied $B_0$ field (Larmor precession) with a certain net magnetization of all nuclei parallel to the $B_0$ field. The rate of precession is called Larmor frequency which is dependent on the specific physical characteristics of the involved nuclei and the strength of the applied $B_0$ field.

By transmitting an RF excitation pulse ($B_1$ field) which is orthogonal to the $B_0$ field, generated by means of an RF transmit antenna or coil, and matching the Larmor frequency of the nuclei of interest, the spins of the nuclei are excited and brought into phase, and a deflection of their net magnetization from the direction of the $B_0$ field is obtained, so that a transversal component in relation to the longitudinal component of the net magnetization is generated.

After termination of the RF excitation pulse, the MR relaxation processes of the longitudinal and transversal components of the net magnetization begin, until the net magnetization has returned to its equilibrium state. MR relaxation signals which are emitted by the relaxation processes, are detected by means of an RF/MR receive antenna or coil. The received MR signals which are time-based amplitude signals, are Fourier transformed to frequency-based MR spectrum signals and processed for generating an MR image of the nuclei of interest within an examination object.

The above RF (transmit and/or receive) antennas can be provided both in the form of so-called body coils (also called whole body coils) which are fixedly mounted within an examination space of an MRI system for imaging a whole examination object, and as so-called surface or local coils which are arranged directly on or around a local zone or area to be examined and which are constructed e.g. in the form of flexible pads or sleeves or cages like head coils.

Further, interventional instruments or medical devices are frequently used during the examination or treatment of an examination object and especially of a local zone or area thereof. Such instruments or devices are for example catheters, biopsy needles, pointers and other which are used for example for biopsies, thermal ablations, brachytherapy, slice selection and other invasive or non-invasive purposes.

Both the above mentioned interventional and non-interventional instruments are usually connected by means of an RF transmission line (especially in the form of an electrically shielded line like a coaxial line) or a cable (which is usually unshielded) comprising at least one electrical conductor like a wire or a strip lines (which are applied onto a carrier like a printed circuit board), with related RF transmitter units, MR receiver units, or other signal processing or control units. It is generally known, that all these RF transmission lines and cables are subject to heating when they are guided through the examination space of an MR imaging apparatus and are exposed during the examination or imaging of an examination object to the transmitted RF excitation field. Such a heating is especially caused by resonant RF common mode currents which are induced in the RF transmission line or cable by the RF excitation field.

Several solutions (like e.g. a mechanical segmentation of the conductors) have been proposed in order to suppress standing waves and to avoid or minimize such a heating and to provide a so called "MR-safe" connection line.

U.S. Pat. No. 5,332,990 discloses a high-frequency safety fuse which comprises a fusible conductor which in its cross-section has a dimension in at least one direction which is substantially twice the penetration depth of the RF current. This fuse is disclosed to be suitable for use in an MR tomographic apparatus for the purpose of protecting the patient against topically excessive RF loads in a local coil circuit.

SUMMARY OF THE INVENTION

It has been revealed that resonant RF common mode currents which are induced by an RF excitation field of an MR imaging apparatus in an RF transmission line or cable which is fed within a catheter (i.e. usually between a hand-piece of the catheter and electrodes or tracking coil(s) etc. at the distal tip of the catheter) or which are induced in an RF transmission line or cable between the hand-piece of the catheter and related remote operating units like RF/MR transmit/receive units or other signal processing units can cause severe heating of the catheter, especially of its distal tip, and of the RF transmission line or cable itself. Further, it has revealed that this heating can be strongly dependent on the position of the catheter and of the RF transmission line or cable, respectively, partly or totally within a surrounding medium of an examination object or a position outside the same.

However, this problem is not limited to catheters, but applies generally in case of elongated electrically conductive objects or structures like guide wires, pacemaker leads, implanted electrodes and other, again especially of their distal end or tip, that may interact with the electromagnetic RF excitation fields inherent to the MR imaging technique.

As mentioned above, in order to avoid such a heating which can harm a patient, it is known to provide a so called MR safe transmission line (STL) which is for example segmented in order to suppress standing wave common mode currents. However, such MR safe transmission lines are usually very complex, bulky and expensive and are not always and under any circumstances as reliable as desired, or they do not allow a desired broadband transmission of RF signals or have other disadvantages.

An object underlying the invention is to find a solution for this problem and to provide an interventional or non-interventional instrument with an RF transmission line or cable such that an increased MR safety in the sense above is obtained, so that a heating of the instrument or of the connected RF transmission line or cable due to resonant RF common mode currents which are induced by an RF excitation field generated by an MR imaging apparatus in an examination space is reliably prevented or at least decreased.

This object is solved according to claim 1 by an interventional or non-interventional instrument for use during an MR imaging or MR examination of an examination object, the instrument comprising an RF transmission line or cable for connecting the instrument with a signal processing unit, wherein the RF transmission line or cable comprises a plurality of fuses which are serially connected into the RF transmission line or cable, wherein adjacent fuses have a distance from one another which is equal to or shorter than a quarter of an effective wavelength of an RF common mode current which is induced in the RF transmission line or cable when exposed to an RF excitation field of an MR imaging apparatus, and wherein each fuse is selected such that it turns into an at least substantially non-conducting state when the current flowing through the fuse or the temperature of the fuse due to the current flowing through the fuse reaches or exceeds a preset threshold value.

Generally, the invention is based on the insight that not any resonant RF common mode currents necessarily result in a dangerous or undesired heating of the related examination object, and that instead of suppressing these currents, a heating by such currents can effectively be prevented by providing an instrument according to claim 1.

An advantage of this solution is, that such fuses can be realized with a high reliability and simplicity at low costs, and that they do not need much space, so that they are suitable for integration especially into a catheter which usually has a very small cross-section. Further, such fuses do not restrict a broadband transmission of RF signals via the related transmission line or cable.

The dependent claims disclose advantageous embodiments of such an interventional or non-interventional instrument.

It will be appreciated that features of the invention are susceptible to being combined in any combination without departing from the scope of the invention as defined by the accompanying claims.

Further details, features and advantages of the invention will become apparent from the following description of preferred and exemplary embodiments of the invention which are given with reference to the drawings.

DETAILED DESCRIPTION OF EMBODIMENTS

Figure 1:
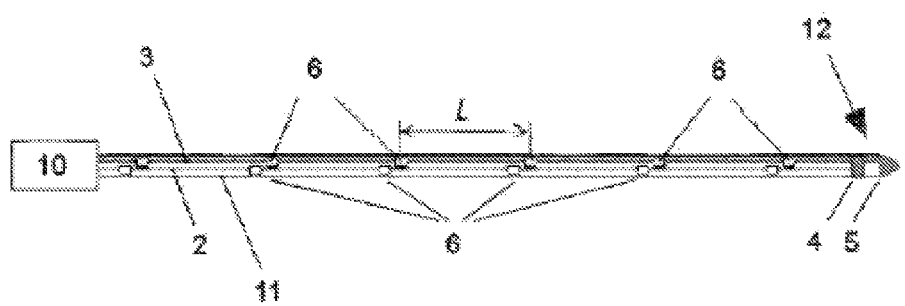
FIG. 1 schematically shows a catheter according to an exemplary embodiment of the invention.

FIG. 1 shows a general configuration of an exemplary embodiment of a catheter according to the invention, which is for example an MR guided EP (electrophysiology) catheter.

The catheter comprises a hand-piece 10, a casing or sleeve 11 and a catheter tip 12. The catheter tip 12 exemplarily comprises a first and a second electrode 4, 5 for conducting e.g. ECG (electrocardiogram) measurements. Additionally or alternatively, a tracking coil (not indicated) for imaging the catheter tip in an MR image and for navigation purposes, a temperature sensor (not indicated) for temperature measurements and possibly other functional units can be provided especially at the tip of the catheter.

For connecting these functional units with the above remote operating units (like RF generators, MR/RF signal receivers and other), usually RF transmission lines or cables are fed inside the catheter between its tip 12 and the hand-piece 10, and between the hand-piece 10 and the said remote units. Exemplarily, FIG. 1 shows a first cable 2 which is connected between the hand-piece 10 and the first electrode 4, and a second cable 3 which is connected between the hand-piece 10 and the second electrode 5. These cables 2, 3 are each realized in the form of a one-wire cable (of course, also one common cable with two wires can be provided), however, instead of such cables, also an RF transmission line for example in the form of a coaxial line or other electrically shielded line could be provided. Such a shielded line is preferably used for feeding RF signals, e.g. for connecting a tracking coil with the hand-piece 10, whereas (unshielded) cables are usually used for connecting said electrodes or e.g. a temperature sensor.

According to the invention, one or preferably both the first and the second cable 2, 3 is provided with a plurality of fuses 6 which are serially connected into each cable. Each fuse 6 is selected such that it releases (and by this at least substantially electrically interrupts the RF transmission line or cable into which it is connected) if a threshold current value through the related fuse is exceeded, which threshold current value is selected such that it results in an unacceptable heating of the related RF transmission line or cable or of the catheter in which the RF transmission line or cable is fed or of the related examination object which is touched by the RF transmission line or cable or the catheter.

Alternatively, each fuse can be selected such that it releases when the temperature of the fuse due to the current flowing through the fuse reaches or exceeds a preset threshold temperature value which is again selected such that it results in an unacceptable heating of the related RF transmission line or cable or of the catheter in which the RF transmission line or cable is fed or of the related examination object which is touched by the RF transmission line or cable or the catheter.

The fuses 6 are preferably realized in the form of melt fuses.

Such a melt fuse can be realized in the form of a known discrete fuse element which is serially connected between adjacent sections of the RF transmission line or cable, or by integrating it into the RF transmission line or cable by locally decreasing the size or area of the cross section of the related RF transmission line or cable. Also both kinds of fuses can be used in one and the same RF transmission line or cable in an arbitrary sequence.

Especially in case of a cable comprising a wire, e.g. a copper wire, or a strip line, such a locally decreased cross section can be obtained for example by locally embossing or stamping at least one of the wires or lines of the cable such that it blows and by this interrupts the cable, if a desired threshold current or a related threshold temperature is exceeded.

Further, the fuses can be realized e.g. in the form of PPTC (polymeric positive temperature coefficient) devices (also called resettable fuses). Such fuses do not melt but release by increasing their electric resistance (i.e. turn into an at least substantially non-conducting state) and by this effectively limit the current (or at least substantially interrupt the RF transmission line or cable into which they are connected) with increasing temperature. These fuses have the advantage that (in contrary to melt fuses) they reset when the current is removed and the temperature decreases so that the related RF transmission line or cable (or catheter, into which these are introduced) need not to be exchanged after release of one or more of the fuses.

Other fuses which fulfill the above function can also be used, wherein one and the same RF transmission line or cable can comprise different kinds of the above and other fuses in an arbitrary sequence.

The fuses are distributed along the RF transmission line or cable preferably at regular intervals. The distance L between adjacent fuses 6 is selected considering the following facts: When the catheter (or any RF transmission line or cable) is exposed to an RF excitation field of an MR imaging apparatus, resonant RF common mode currents are induced in the RF transmission line or cable. The resulting RF current maxima are spaced from one another by half of the effective common mode wavelength in the transmission line or cable. This wavelength is, as generally known, dependent on the dielectric characteristics of the surrounding medium, especially of the examination object, at which or into which a catheter is possibly fed. Depending on a present position of the catheter outside an examination object or partly or totally introduced into an examination object, the effective common mode wavelength varies and the RF current maxima accordingly shift along the transmission line or cable. Further, these maxima can shift depending on an external connection of the transmission line or cable and e.g. the presence of metals parts near to those sections of the catheter or the transmission line or cable, respectively, which are not introduced into an examination object. Consequently, the effective common mode wavelength can vary considerably and is dependent on a certain application environment of the catheter or the transmission line or cable. It can be measured in a laboratory set-up for typical such applications and the related environmental conditions.

The fuses 6 which are positioned along the RF transmission line or cable 2, 3 are spaced apart from one another preferably such that the distance L between adjacent fuses 6 is at least substantially equal to or shorter than a quarter of the shortest effective common mode wavelength which is induced in the RF transmission line or cable when exposed to an RF excitation field of an MR imaging apparatus during an MR imaging or examination, wherein the shortest wavelength is usually the wavelength when the related section of the RF transmission line or cable is fully inserted into the examination object. If certain sections of an RF transmission line or cable are not to be introduced into an examination object but provided for example for connecting the handpiece 10 of the catheter to a related operating unit (not indicated), the shortest effective common mode wavelength is usually longer according to the dielectric properties of the surrounding air. Consequently, it is not necessary, that all distances L between adjacent fuses 6 are the same along the whole length of an RF transmission line or cable.

By such a selection of the distance L of adjacent fuses 6, always at least one of the fuses 6 is positioned at or in the near surroundings of a current maximum and releases, if this current maximum exceeds the above threshold current or if the resulting temperature which increases due to this current maximum exceeds the above threshold temperature.

By such a release of at least one of the fuses, the resonant RF common mode currents are suppressed or limited, so that a further heating of the related RF transmission line or cable and consequently of the catheter, especially of its tip, and consequently of the examination object is effectively prevented or limited.

In case of a melt fuse, the related RF transmission line or cable has to be disposed and replaced by a new one if the melt fuse releases. However, this might be acceptable due to the fact, that melt fuses and by this the related RF transmission line or cable can be realized at comparatively low cost. Further, in case of an interventional device, this is usually provided for single-use only and by this for disposal anyway.

The fuses according to the invention can be used alone or in addition to known solutions for preventing heating by RF induced common mode currents (like for example a segmentation of the cable), in order to increase reliability and safety.

Another advantage especially of a melt fuse is that a certain delay of release can be realized, so that for example a very high but short RF transmission peak which is generated by an MR imaging apparatus and which induces a related peak current in the RF transmission line or cable which exceeds the threshold current value, would not release the fuse, because such a peak current would not increase the temperature at or above the threshold temperature value in the RF transmission line or cable etc. for releasing the melt fuse. By this, the proposed threshold current value for releasing the fuse is not an absolute value but a time-averaged value of a certain current or power delivered in the fuse. In order to obtain this, the fuse can be realized in a known manner in the form of a time-lag or slow acting fuse (in contrast to a quick acting fuse or fast blow fuse).

Generally, and as mentioned above, a fuse can be realized in its simplest form by a thin metal wire which melts if the threshold current/temperature value is reached or exceeded. Such fuses can be incorporated into the RF transmission line or cable as discrete components, especially in the form of conventional melt fuses of substantially any type.

However, especially in case of a cable or metal wire, for example as those which are used inside an EP-catheter, the fuses can be integrated into each single wire by making the wire locally thinner, i.e. by reducing the area or size of the cross section of the wire.

This can be obtained in a simple way by stamping or embossing the wire by means of a dedicated tool and by this by effectively creating the fuse from the original wire itself. Usually, such wires are covered with an electrically insulating layer especially in the form of a thin varnish. In such a case, either the stamping or embossing process is conducted before the insulating layer is applied onto the wire, or the insulating layer is an elastic layer and/or the tool is appropriately shaped such that the layer is not damaged by the stamping or embossing process.

When realizing such an integrated melt-type fuse or selecting a conventional separate such fuse, it should preferably be ensured that the gap after the melting of the fuse is long enough to prevent the generation of sparks over the gap. Generally, it should preferably further be ensured that the stray capacitance of the open fuse is smaller than about 10 pF in order to represent a high enough RF impedance at the open fuse.

In general, the fuses can be incorporated into any type of RF transmission line or cable for any interventional on non-interventional device which is provided or adapted for use in an MR imaging apparatus during MR imaging of an examination object. Another example of such a device is an active tracking catheter which is of great relevance to most vascular MR interventions. Usually, an active tracking catheter contains one or more MR-tracking coils for receiving MR signals which are evaluated in a known manner to localize the tracking coil and thus the respective part of the catheter in an MR image of an examination object.

Usually, such a tracking coil is positioned at the tip of the catheter, so that a cable connection inside the catheter between the tracking coil and the hand-piece of the catheter is required for the transmission of the received MR signals. Preferably, coaxial cables having a diameter of for example 0.5 mm or less (micro-coaxial cables) are used for such a cable connection.

Figure 2:
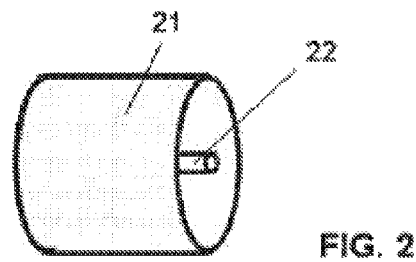
FIG. 2 schematically shows a coaxial fuse according to a first embodiment of the invention.

The fuses which are serially connected into such a coaxial cable are preferably provided such that reflections of the MR signal, especially due to a mismatching of the impedance of the cable and the impedance of the fuses are avoided. This can be achieved by realizing a coaxial fuse structure according to FIG. 2 which comprises an inner central fusing wire (conductor) 22 which connects the adjacent ends of the center leads of the coaxial cable, and an outer cylindrical fusing component (conductor) 21 which surrounds the central fusing wire 22 and which connects the adjacent ends of the shields of the coaxial cable. Further, between the central fusing wire 22 and the surrounding cylindrical fusing component 21, preferably an insulator material is provided so that the structures of the coaxial fuse and of the coaxial cable correspond with each other and by this a related mismatching is minimized.

It has revealed that for realizing such a coaxial fuse, the following issues are preferably considered: RF current values which are associated with a considerable heating especially at the tip of an active interventional instrument like a catheter have been shown to be in a range of between about 0.1 A and 1 A, wherein the higher this value is, the quicker a fuse should release (i.e. blow) in order to avoid a dangerous or undesired degree of heat deposition in an examination object.

Assuming that the above RF current range is defined as a current threshold range, it has revealed that the fuse should release or blow within a time duration in the order of about one second after this threshold range is reached in order to reliably avoid such an undesired heat deposition.

The time $T_m$ to melt the outer cylindrical fusing component 21 of a coaxial fuse can be estimated by the ratio of the heat Q required to melt this component 21 to the power P dissipated by the current I as follows:

$$T_m = \frac{Q}{P} = \frac{c_m m(T_s - T_0)}{RI^2} = \frac{c_m \rho_m (T_s - T_0) A^2}{I^2 \rho_e}$$

with $c_m$=specific heat per unit mass, $\rho_m$=mass density, $T_s$=melt point, $T_0$=body temperature, A=cross sectional area of the lead, and $\rho_e$=specific resistance.

The outer cylindrical fusing component 21 of a coaxial fuse will tend to have a larger cross section than the central fusing wire 22. Thus, the time duration to melt the outer cylindrical fusing component 21 will be longer than to melt the central fusing wire 22.

In case of a coaxial fuse with a total thickness of about 300 μm and a layer thickness of the metallic outer cylindrical fusing component 21 of about 10 μm, the melting time Tm given in seconds in case of a current of about 1 A is for different materials of the outer cylindrical fusing component 21 as follows:

$$MK_{n,4} = \begin{pmatrix} "Al" \\ "Bi" \\ "Cu" \\ "Au" \\ "Pt" \\ "Ag" \\ "Tin" \\ "Zinc" \end{pmatrix}$$

$$Tm = \begin{pmatrix} 4.782 \\ 0.021 \\ 18.634 \\ 9.299 \\ 4.321 \\ 12.765 \\ 0.25 \\ 1.616 \end{pmatrix}$$

Figure 3:
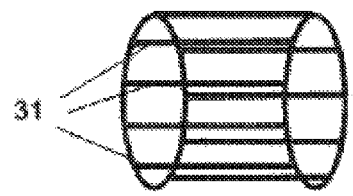
FIG. 3 schematically shows a coaxial fuse according to a second embodiment of the invention.

If shorter melting times or lower current thresholds are required, an outer cylindrical fusing component 31 can be implemented according to FIG. 3 in the form of a plurality of parallel thin wires which are arranged on a surface of a cylinder and parallel to the longitudinal axis of the cylinder so that the cross section of the outer cylindrical fusing component 31 is further reduced. In FIG. 3, the central fusing wire is not indicated for clarity reasons only.

However, due to the fact that nevertheless the melting time of the central fusing wire will even be shorter, it need not to be considered, but only the melting time of the outer cylindrical fusing component 21, 31, if it is desired to completely interrupt a coaxial transmission line.

Apart from the above active tracking catheters the fuses according to the invention can also be incorporated into MR-EP catheters for RF ablation. Such catheters usually also include at least one of a tracking coil, a temperature sensor and ECG electrodes, which all have to be connected by means of an RF transmission line, especially a coaxial line or one or two wires or cables within the catheter with a hand-piece. These RF transmission lines and cables can also be provided with fuses as explained above. Regarding the cable for supplying RF ablation power, a fuse according to the invention is usually not applicable due to the comparatively high RF currents required for RF ablation. Such cables are made RF-safe in a known manner e.g. by segmenting the cable mechanically.

Fuses according to the invention can also be applied in other interventional devices like implants. However, due to the fact that the necessity of replacement of such an implant in case of a blown melt fuse is considered detrimental, the fuse according to the invention is preferably a resettable fuse as mentioned above, or is used as a "last safety measure" in a redundant system of several safety measures for preventing heating by RF induced common mode currents.

Further, an RF transmission line or cable according to the invention can also be provided for connecting the hand-piece of a catheter with a related MR receiver or another signal processing unit for operating a tracking coil, ECG electrodes or temperature sensors etc. within the catheter. However, because a comparatively large diameter of such cables is usually not detrimental and/or the replacement of such cables may be undesired and costly, the fuses according to the invention can again at least be used as a last safety measure in a redundant system for preventing heating by RF induced common mode currents as mentioned above. The same accordingly applies for other interventional or non-interventional instruments like local coils, surface coils, head coils, other surgical devices, biopsy needles, pointers and other.

While the invention has been illustrated and described in detail in the drawings and foregoing description, such illustration and description are to be considered illustrative or exemplary and not restrictive, and the invention is not limited to the disclosed embodiments. Variations to embodiments of the invention described in the foregoing are possible without departing from the scope of the invention as defined by the accompanying claims. Variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. The mere fact that certain measures are recited in mutually different dependent claims does not indicate that a combination of these measured cannot be used to advantage. Any reference signs in the claims should not be construed as limiting the scope.

The invention claimed is:

1. An instrument for use during magnetic resonance imaging, the instrument comprising:
   cable for connecting the instrument with a signal processing unit,
   wherein:
   the cable comprises a plurality of fuses that are connected in series to the cable,
   adjacent fuses have a distance from one another that is equal to or shorter than a quarter of an effective wavelength of an radio frequency common mode current that is induced in the cable when exposed to radio frequency excitation field of a magnetic resonance imaging apparatus, and
   each fuse is selected such that it turns into an at least substantially non-conducting state when the current flowing through the fuse exceeds a threshold or when the temperature of the fuse due to the current flowing through the fuse reaches or exceeds a threshold value.

2. The instrument of claim 1, wherein the fuses are melt fuses.

3. The instrument of claim 1, wherein the fuses are integrated into the cable in the form of a local reduction of the size or area of the cross section of the cable.

4. The instrument of claim 1, wherein the fuses are realized in the form of discrete fuse elements.

5. The instrument of claim 1, wherein the fuses are realized in the form of a time-lag fuse or a slow acting fuse.

6. The instrument of claim 1, wherein the cable is a coaxial line and the fuses are realized in the form of a coaxial fuse comprising a cylindrical outer conductor and an inner central conductor.

7. The instrument of claim 6, wherein the cylindrical outer conductor is a cylindrical foil.

8. The instrument of claim 6, wherein the cylindrical outer conductor is provided by a plurality of wires which are arranged parallel to each other on a surface of a cylindrical and parallel to the longitudinal axis of the cylinder around the inner central conductor.

9. The instrument of claim 1, wherein the cable comprises at least one electrically conducting wire into which the fuses are serially connected.

10. The instrument of claim 1 in the form of a catheter, the catheter comprising a hand-piece, a casing and at least one of a tracking coil, a temperature sensor and electrocardiography electrodes within the casing, wherein the cable is guided within the casing for electrically connecting at least one of the tracking coil, temperature sensor and electrocardiography electrodes with the hand-piece.

11. The instrument of claim 10, wherein the cable is provided for connecting the hand-piece with a remote signal receiving and/or a remote signal processing unit.

12. The instrument of claim 1 is selected from the group consisting of a catheter, a surgical device, a biopsy needle, a pointer, a local coil, a surface coil, a head coil, wherein the cable is provided for connecting the instrument with a remote signal receiving and/or remote signal processing unit.

13. A magnetic resonance imaging system comprising the instrument of claim 1.

14. The instrument of claim 1, wherein the fuses are resettable fuses.

15. The instrument of claim 14, wherein the fuses are polymeric positive temperature coefficient (PPTC) devices.

* * * * *